(12) United States Patent
Tomt et al.

(10) Patent No.: US 7,449,336 B2
(45) Date of Patent: Nov. 11, 2008

(54) TEST FOR SOL-GEL ON ALUMINUM RIVETS

(75) Inventors: Terry C. Tomt, Enumclaw, WA (US); Bruce R. Davis, Seattle, WA (US); Steven R. Jones, Sumner, WA (US); Richard G. Wire, Bonney Lake, WA (US)

(73) Assignee: The Boeing Company, Chicago, IL (US)

( * ) Notice: Subject to any disclaimer, the term of this patent is extended or adjusted under 35 U.S.C. 154(b) by 824 days.

(21) Appl. No.: 10/762,073

(22) Filed: Jan. 20, 2004

(65) Prior Publication Data

US 2005/0158862 A1 Jul. 21, 2005

(51) Int. Cl.
*G01B 11/06* (2006.01)
(52) U.S. Cl. .......................................... 436/5; 436/166
(58) Field of Classification Search ................. 436/136; 250/341.8; 252/389.31; 428/402, 461, 343
See application file for complete search history.

(56) References Cited

U.S. PATENT DOCUMENTS

| | | | | |
|---|---|---|---|---|
| 5,562,989 | A | * | 10/1996 | Statz .......................... 428/402 |
| 5,674,698 | A | * | 10/1997 | Zarling et al. ............... 435/7.92 |
| 5,814,137 | A | | 9/1998 | Blohowiak et al. |
| 5,849,110 | A | | 12/1998 | Blohowiak et al. |
| 5,869,140 | A | | 2/1999 | Blohowiak et al. |
| 5,869,141 | A | | 2/1999 | Blohowiak et al. |
| 5,939,197 | A | | 8/1999 | Blohowiak et al. |
| 5,958,578 | A | | 9/1999 | Blohowiak et al. |
| 6,037,060 | A | | 3/2000 | Blohowiak et al. |
| 6,177,189 | B1 | * | 1/2001 | Rawlings et al. ............. 428/343 |
| 6,579,472 | B2 | * | 6/2003 | Chung et al. ............ 252/389.31 |
| 2003/0230719 | A1 | | 12/2003 | Shelley et al. |

FOREIGN PATENT DOCUMENTS

| | | |
|---|---|---|
| SU | 1 368 719 A | 1/1988 |
| WO | WO 2004/033115 A | 4/2004 |

OTHER PUBLICATIONS

Haixing Z et al.: "*An Alternative to Anodization: Sol-Gel Solutions for Metal Finishing*", Metal Finishing, Metals and Plastics Publications, Hackensack, NJ, vol. 96, No. 12, Dec. 1998, pp. 35-36, 38.
European Search Report dated Aug. 8, 2005, Appl. No. 04078401.9-2204.

* cited by examiner

*Primary Examiner*—Walter D Griffin
*Assistant Examiner*—Christine T Mui
(74) *Attorney, Agent, or Firm*—Duke W. Yee; Dennis R. Plank; Theodore D. Fay, III

(57) ABSTRACT

A method for testing for the presence of sol-gel on an aluminum test specimen includes: preparing an ammonium molybdate solution; preparing a hydrochloric acid solution; and mixing the solutions in 2:1 ratio in each of a number of receptacles. A test specimen of unknown coating, a first control specimen, and a second control specimen are placed in the mixed solution in three receptacles. The first control specimen has a sol-gel coating over an alodine coating; and the second control specimen has an alodine only coating. By timing events such as a change in color of the test and control specimens or the solution becoming opaque, the method determines that the test specimen of unknown coating has a like coating to that of a particular one of the control specimens if the timing of the event of the test specimen and the timing of the event of the particular control specimen are comparable.

32 Claims, 1 Drawing Sheet

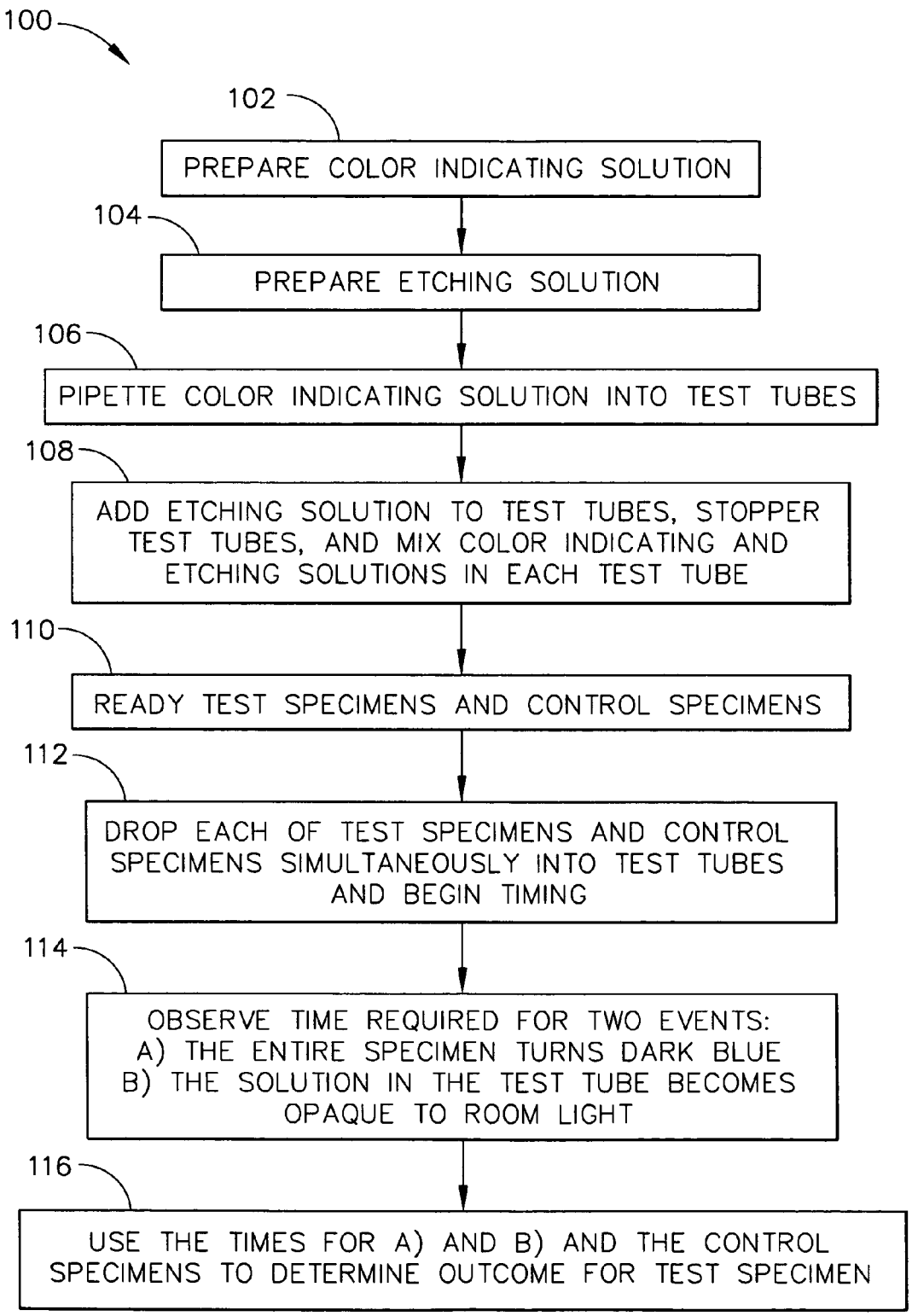

TEST FOR SOL-GEL ON ALUMINUM RIVETS

BACKGROUND OF THE INVENTION

The present invention generally relates to tests for the presence of chemical substances and, more particularly, to a novel test for the presence of sol-gel on aluminum.

Aluminum surfaces in aircraft, particularly on fasteners such as rivets, are typically coated at some stage during the manufacturing process with some kind of protective or adhesion promoting coating, called a conversion coating. Chromate conversion (such as 'ALODINE® or IRIDITE®') is a chemical treatment process for aluminum used to provide corrosion protection and surface preparation for paint and adhesives. There are a wide variety of conversion coatings, widely known in the industry generically as "alodine" coatings. Alodine coatings have been in wide use in the aircraft and aerospace industries since the 1950's. For example, various forms of alodine may include chromic acid or chromium trioxide or hexavalent chromium. There are a number of different formulations of alodine—such as 'ALODINE 600, ALODINE 1000, ALODINE 1200S, ALODINE 1600 AND IRIDITE 14-2' for example—that are commercially available from a large number of suppliers.

Conversion coatings are commonly used to protect rivet fasteners in the aerospace industry. Conversion coatings are typically used to protect the parts—for example, rivets—during storage prior to installation. Protection may be required, for example, to prevent corrosion of the aluminum surface of parts. Depending on the processes used, the conversion coating may also be used to provide an appropriate base on which to adhere paint.

"Rivet rash" refers to the loss of paint from aluminum rivet heads on in-service aircraft. Rivet rash is a serious problem that can greatly detract from an aircraft's appearance and airlines, especially, tend to be concerned over the detraction from decorative appearance in areas most visible to the passengers, in particular, the nose section and entry doors of aircraft. In addition, rivets can "rash" within six months of delivery giving the airplane a prematurely older appearance. The problem has been exacerbated by the introduction of newer, environmentally safer paints.

Because the presence or absence of conversion coatings is not always easily detectable, tests have been developed for them to verify whether or not the coatings are present on parts when, for example, there may be some reason for doubt or, for example, a part needs to be double-checked during a manufacturing process.

Due to problems with paint adhesion, aircraft manufacturers are developing new coatings and processes to improve paint adhesion on exterior aluminum surfaces, and especially for aluminum rivet heads. Some of the new coatings are clear and extremely thin, thus requiring special tests for the verification of their presence before parts are installed.

As can be seen, there is a need for a test to determine whether these new coatings are present or absent on aircraft parts. Moreover, there is a need for a quick, easy, and reliable way to verify that aluminum rivets have been coated with these new coatings after they arrive from the manufacturer.

SUMMARY OF THE INVENTION

In one aspect of the present invention, a method for testing for the presence of a coating includes a step of testing for the presence of a sol-gel coating, which is a type of coating that is newly used for improving paint adhesion, for example, on rivets.

In another aspect of the present invention, a method for testing for the presence of a coating includes steps of: placing a mixed solution in a receptacle; placing a test specimen of unknown coating in the receptacle; and timing an event to make a determination of whether or not the coating is present.

In still another aspect of the present invention, a method for testing for the presence of a coating on aluminum includes steps of: mixing an indicating solution and an etching solution in a number of receptacles to form a mixed solution in the receptacles; placing a test specimen of unknown coating in a first receptacle of the receptacles; placing a control specimen in a second receptacle of the receptacles; and timing a number of events to make a determination of whether or not the coating is present on the test specimen.

In yet another aspect of the present invention, a method for testing for the presence of sol-gel on an aluminum test specimen includes steps of: preparing fresh, weekly, an indicating solution by adding 10 g of ammonium molybdate, 4-hydrate in 100 ml of water; preparing an etching solution by adding hydrochloric acid (HCl) in 1:1 ratio to water; using a pipette to place 4 ml of the indicating solution into each of a number of receptacles; adding 2 ml of the etching solution to each of the receptacles; and mixing the indicating solution and the etching solution in each of the receptacles to form a mixed solution in each of the receptacles. Those steps are followed by: placing a test specimen of unknown coating in the mixed solution in a first receptacle; placing a first control specimen in the mixed solution in a second receptacle; and placing a second control specimen in the mixed solution in a third receptacle. The test specimen, the control specimen, and the second control specimen are aluminum rivets of the same size, type and alloy. The first control specimen has sol-gel applied over an alodine coating; and the second control specimen has an alodine only coating. The method continues with: timing a plurality of events including: a change in color of the entire test specimen to dark blue; a change in color of the entire first control specimen to dark blue; and a change in color of the entire second control specimen to dark blue. The method concludes by determining that the test specimen of unknown coating has a like coating to that of the first control specimen if the timing of the change in color of the entire test specimen to dark blue and the timing of the change in color of the entire first control specimen to dark blue are comparable; and determining that the test specimen of unknown coating has a like coating to that of the second control specimen if the timing of the change in color of the entire test specimen to dark blue and the timing of the change in color of the entire second control specimen to dark blue are comparable.

In a further aspect of the present invention, a method of testing for the presence of a coating of sol-gel, alodine, or sol-gel over alodine on an aluminum aircraft part includes the steps of: (A) immersing the aluminum aircraft part in a first solution of ammonium molybdate and etching solution; (B) measuring a first time required for a visual change to occur; and (C) comparing the first time to a second time required for a similar visual change to occur when an aluminum aircraft part having a known coating of sol-gel, alodine, or sol-gel over alodine is immersed in a second solution having the same composition as the first solution.

In a still further aspect of the present invention, a test solution comprises an ammonium molybdate solution and a hydrochloric acid solution.

In yet a further aspect of the present invention, an indicating/etching solution comprises an ammonium molybdate solution and a nitric acid.

These and other features, aspects and advantages of the present invention will become better understood with reference to the following drawings, description and claims.

BRIEF DESCRIPTION OF THE DRAWINGS

The FIGURE is a flowchart diagram showing a summary of a method for testing for the presence of a coating on a metal part according to one embodiment of the present invention.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, one embodiment of the present invention provides a test for the presence of sol-gel coatings on metal surfaces, such as aluminum. Sol-gel is a chemical substance with good adhesion properties that make it useful as a conversion coating for rivet heads while providing a base for paint adhesion. Sol-gel coatings for metal and metal alloys are disclosed, for example, in U.S. Pat. No. 5,939,197, issued Aug. 17, 1999, and U.S. Pat. No. 6,037,060, issued Mar. 14, 2000, both of which are incorporated by reference. The term "sol-gel," a contraction of solution-gelation, refers to a series of reactions where a soluble metal species (typically a metal alkoxide or metal salt) hydrolyze to form a metal hydroxide. The soluble metal species usually contain organic ligands tailored to correspond with the resin in the bonded structure. The metal hydroxides condense (peptize) in solution to form a hybrid organic/inorganic polymer. Depending on reaction conditions, the metal polymers may condense to colloidal particles or they may grow to form a network gel. The ratio of organics to inorganics in the polymer matrix may be controlled to maximize performance for a particular application. Many metals are known to undergo sol-gel reactions. Silicon and aluminum sol-gel systems have been studied extensively.

Because a sol-gel coating, which is typically transparent, may not be visible to the naked eye, there is a need for being able to conveniently detect the presence of sol-gel coatings. Such a need arises, for example, for purposes of quality control in industry where a number of identical parts—such as aluminum rivet fasteners or other metal fittings—may be delivered from suppliers in batches, where it may be that some batches are specified to be coated with sol-gel and some are not so that verification or checking may become necessary or desired. Or, using rivets as an example, it may be desired to verify by means of random sampling that each delivery of sol-gel coated rivets actually are coated with sol-gel before committing to installation on aircraft, where removal of erroneously installed non-coated parts could cause disastrous expense and delays in manufacturing schedule. Another possibility is that different batches of parts or fasteners could become "mixed up" on the shop floor, necessitating testing before use of the parts. For these and a multitude of other possible situations, it is desired to have a convenient, fast, easy to use test that can be performed to test for the presence of sol-gel and possibly other coatings on parts made of aluminum.

One sol-gel coating that can be tested for, for example, is 'BOEGEL-EP II' sol-gel coating, The test, according to an embodiment, may be extremely useful in the aerospace industry where it is desired, for example, to have a test for the presence of sol-gel coatings, which typically are invisible to the naked eye, on fasteners such as rivets, where it is desired to ensure the presence of sol-gel on the rivet heads in order to provide good paint adhesion. Good paint adhesion is desirable, for example, on rivet heads located on the exterior painted surface of aircraft where a problem known as "rivet rash"—the selective loss of paint from exposed rivet heads—is sought to be alleviated by coating the rivets with sol-gel prior to the application of paint. The sol-gel coating may be applied over an alodine coating. The alodine coating may be "leached" prior to coating with sol-gel, which simply means that the alodine coating is soaked in heated water to remove its characteristically brownish color (making it more or less transparent) in order to improve its aesthetic qualities in view of the later application of paint, since the sol-gel (which covers the alodine) is also generally transparent.

In one embodiment, the test distinguishes rivets having a coating of only leached alodine (which may be a clear coating) from rivets having a coating of sol-gel over leached alodine (which may also be a clear coating). In one embodiment, the test can also distinguish bare rivets from those coated with alodine or those coated with sol-gel. In fact, because the test may normally be used, for example in the context of quality control described above, the specimen (e.g. rivet) to be tested may usually be known to have one of a limited number of types of coating present. The test can provide a control specimen of each type of coating for comparison to the test specimen. The test may use a mixed etching and indicating solution into which test and control specimens are individually and separately immersed. The solution turns blue because of a reaction with the aluminum of each specimen, and not because of a reaction with the sol-gel. So, for example, if you were to put a glob of sol-gel into the solution, it would generally not turn blue. Thus, the mixed solution takes longer to turn blue if the aluminum is coated with anything that the solution cannot etch quickly through. Test and control specimens could be coated with superglue, epoxy, or something else that is not attacked or attacked slowly by the solution. The test would then tell you that there is an impervious coating, but it would not necessarily tell you that the coating is sol-gel unless the test has been limited to sol-gel as one of the alternatives beforehand. Thus, so long as the test specimen is known to have one of a limited number of types of coating and so long as the appropriate control specimens are used, one embodiment can be used to test not only for sol-gel, but potentially for a wide range of different types of relatively impervious coatings.

Sol-gel is a relatively new coating process where the application of paint to aircraft is concerned, tests which are new compared to tests for alodine coatings or for scratches in clad aluminum (e.g. tests for integrity of the coating), which have existed for some time. Embodiments of the present invention differ from the prior art in that, for example, no convenient, fast, easy to use, chemical test for the presence or absence of sol-gel is known to exist in the prior art, even though prior art tests exist for detecting the presence on aluminum of, for example, alodine only coatings and anodized coatings. The prior art tests are typically spot tests—in which, typically a "drop" of solution is placed on a test sample to create a "spot" on the sample for observation—whereas a test according to one embodiment of this invention may be an immersion test—in which test samples are immersed in solution for observation. In one embodiment, the test may work on any aluminum surface, to distinguish the presence or absence of sol-gel. The test of one embodiment of this invention may be performed on any form of aluminum, including pure or alloyed aluminum, anodized aluminum, chemically or manually deoxidized, or burnished aluminum, in any shape or form including sheets, rivets, bolts, extruded, molded, or formed parts, so long as an immersible test sample and identical (e.g. size, shape, composition, and surface treatment) immersible control samples with known coatings can be obtained.

Also, for example, in contrast to the prior art, one embodiment may use hydrochloric acid instead of the nitric acid commonly used for prior art tests not directed toward detecting sol-gels. Additionally, for example, the test method according to one embodiment is unique compared to the prior art in that: (1) the test method may utilize a specific timed exposure range to the chemical solution, and (2) the test method may compare the color results between a known control and the unknown test parts.

The following procedure illustrates one example of a chemical spot test for detecting alodine coatings:

Solution A:
  Dissolve 0.1 gram (g) potassium chloride (KCl) in 50 milliliters (ml) of water.
  Add 1 to 6 ml of concentrated nitric acid, ($HNO_3$)
Solution B:
  Dissolve ammonium molybdate $(NH_4)_6Mo_7O_{24}$ 3.0 g in 50 ml of water.
  Add 1 ml of concentrated $NH_4OH$.
  Heat to boiling and cool.
Procedure:
  Place a drop of solution A on the part being checked for Alodine, followed by a drop of solution B.
  Disregard any white precipitant which may form and re-dissolve.
  If the part is not alodined, a blue spot will appear on the surface of the aluminum within 1 minute.

Although the above test for alodine uses an ammonium molybdate solution (solution B), it is designed to be relatively specific for detection of alodine coatings and not for detection of coatings in general. For example, using the combination of ammonium molybdate and nitric acid, as in the above spot test, the above spot test will not work at all for detecting sol-gel. The above spot test for alodine coatings appears to rely on the fact that alodine is soluble in nitric acid if you wait long enough. Sol-gel, however, is not soluble in nitric acid, nor does an ammonium molybdate solution by itself work for detecting sol-gel on aluminum. A proper combination of ammonium molybdate solution with the right acid is required to provide a working test for sol-gel, which has not been found by using or adapting any other tests.

In an alternative embodiment, however, a combination of ammonium molybdate and nitric acid may be used as the mixed solution, or etching/indicating solution to discriminate between sol-gel coated rivets and those that are leached alodine coated or not coated at all. For example, a sol-gel coated rivet that is dropped into molybdate/nitric acid etching/indicating solution will not etch and, thus, not turn blue within any practical length of time. By the same token, a bare rivet or leached alodine coated rivet may react and turn dark blue in molybdate/nitric etching/indicating solution due to there being no sol-gel protection layer. Thus, by comparing the time for control specimens to either turn blue or not turn blue, as in the comparison described below for event a), a molybdate/nitric etching/indicating solution may be used in an alternative embodiment of the present invention.

In one embodiment of this invention, an indicating solution, which may be ammonium molybdate solution, for example, in combination with an etching solution, which may be, for example, hydrochloric acid solution, may be used for the detection of sol-gel coatings on aluminum. The ratio of indicating (ammonium molybdate) solution to etching (hydrochloric acid) solution in the combination may be important. In one embodiment, a combination with a ratio of ammonium molybdate solution to hydrochloric acid solution of 4:2 (by volume, when the solutions are prepared as described below in steps 102 and 104) may provide a working test for the detection of sol-gel coatings on aluminum. Different ratios may work, and the specific ratio used may affect the time resolution of the test, i.e., the ability of the test to distinguish between the coatings on the test and control sample specimens based on the amount of time required to observe certain events. The amount of time may depend, for example, on the amount of time required for a test solution to etch through a sol-gel or other coating and reach the substrate surface, which may be aluminum, for example, followed by an amount of time required for the test solution to react with the substrate, for example, to provide an observable event such as a change in the color of the samples or opaqueness of the test solution. Other factors may also affect the time resolution of the test. For example, thinner sol-gel coatings may take less time in general and thicker sol-gel coatings may take more time in general for either the test specimen to change color or the test solution to become opaque.

A ratio of ammonium molybdate solution to hydrochloric acid solution of greater than about 4:1 (4 ml to 1 ml by volume, when the solutions are prepared as described below in steps 102 and 104) may, for example, not provide a working test, as the test solution may turn a milky white with a solid white precipitate forming, and the whole test tube may solidify.

Also for example, a ratio of ammonium molybdate solution to hydrochloric acid solution of less than about 1:1 (3 ml to 3 ml by volume, when the solutions are prepared as described below in steps 102 and 104) may be too aggressive (e.g. etching too fast through the sol-gel of a test or control sample) so that there may not be enough spread in the times of observable events to distinguish between coated and uncoated samples, i.e., the time resolution of the test, as described above is adversely affected. Also, for example, at the 3:3 ratio, the test solutions may turn aluminum rivet samples more yellowish brown instead of blue, which may confound the test as the blue color is more easily distinguishable as a definite change in color.

Referring now to the FIGURE, a method 100 is illustrated for testing for the presence of sol-gel on aluminum in accordance with one embodiment. The method may include steps 102 through 116, as shown in the FIGURE, for performing a test according to method 100. The test according to method 100 may normally be performed at any comfortable room temperature, for example, between about 65° F. and about 80° F. and may be expected to work in a temperature range that may include from about 40° F. to about 110° F. For example, if the test is performed at too warm a temperature, it may be expected that the increased temperature will speed up the etching reaction of the test solution and the test may lose time resolution, described above. On the other hand, for example, if the test is performed at too cool a temperature, it may be expected that the coolness may increase the time resolution, but the test may become inconvenient or wasteful as the time required to obtain test results increases and may increase beyond what is needed for dispositive results. It should be noted that the use of control samples, in accordance with one embodiment, may remove the specific temperature as a factor affecting the results of the test. The test according to method 100 may normally be performed at room temperature and without stirring or shaking of the test tubes during the test.

Ammonium molybdate may react with the aluminum of the test and control specimens (e.g. rivets) to form a blue compound. The hydrochloric acid may etch through the coatings on the specimens (rivets) and allow the ammonium molybdate to react with the aluminum of the specimen.

At step 102, an indicating solution may be prepared. For example, prepare 10 g in 100 ml water of ammonium molybdate, 4-hydrate. $((NH_4)_6Mo_7O_{24}\cdot 4H_2O)$. For example, ammonium molybdate is commercially available as a powder, which may be available in a number of grades, depending on the amount of water present, the dryer powders being more expensive and wetter powders less expensive. For the purpose of tests according to an embodiment of the present invention, a less expensive grade containing more water, such as ammonium molybdate, 4-hydrate, may be acceptable. For better results, the indicating solution may be prepared fresh weekly.

At step 104, an etching solution may be prepared. For example, prepare 1:1 HCl, i.e., hydrochloric acid in a one-to-one ratio with water, by adding the acid to water. For example, HCl is usually sold as a solution, typically at about 37% or less, referred to here as concentrate. The etching solution may be prepared as just described by adding the concentrate to water until a one-to-one ratio (by volume) of the concentrate to water is achieved. Other ratios of concentrate to water may be used but, in general, the same effects may be achieved by changing the ratio of indicating solution to etching solution, as described above.

At step 106, the indicating solution—such as the solution prepared at step 102—may be placed into one or more receptacles, which may be test tubes, for example. It may be preferable to use a test specimen and two control specimens with one receptacle for each specimen, so that at least three receptacles may be prepared for one specimen of unknown coating to be tested. For example, pipette 4 ml of ammonium molybdate, 4-hydrate into each of three glass test tubes, which for testing rivets may conveniently be of a size 13×100 mm.

At step 108, the indicating solution and the etching solution may be mixed together to form mixed solution, which may be placed in the receptacles. For example, add 2 ml of 1:1 HCl (etching solution) to each test tube; insert a rubber stopper in each test tube, and mix each test tube. Thus, the proportion of indicating solution to etching solution may be in the ratio of 4 ml (step 106) to 2 ml (step 108) or 2:1. In an alternative embodiment, as described above, the mixed solution may be mixed as a molybdate/nitric acid etching/indicating solution.

At step 110, the test and control specimens may be readied for the test. One or more test specimens may be tested at the same time, along with two known control specimens to effectively "calibrate" the results of the test. Thus, at least three specimens would usually be used to perform the test. In order to eliminate extraneous factors from the test, the test and control specimens should be of the same size, type, shape, and composition. For example, gather together three rivets of the same size and type for the test—one rivet known to be coated only with leached alodine (a control specimen), one known to be coated with leached alodine plus sol-gel (a control specimen), and one unknown rivet (a test specimen of unknown coating). It should be noted that the test and control rivets should all be of the same alloy. For example, the test may be especially useful in the aerospace industry for rivets known as type GF and FV, which are manufactured of 2000 and 7000 series aluminum, respectively.

At step 112, each of the specimens may be placed in the mixed solution and timing of the events, described below, may begin. For example, the specimens may all be placed in the receptacles containing mixed solution simultaneously with the start of a timer to time all the specimens at one time. Alternatively, each specimen could be timed individually. Any reasonably accurate timing device, such as a stopwatch, for example, may be used. For example, simultaneously drop each of the three rivets—such as the test specimen and two control specimens referred to above—into respective test tubes and begin timing events with a stopwatch.

At step 114, for each of the specimens (and each receptacle) observe the time required for either or both of two events to happen:

a) The entire specimen (e.g. rivet) changes color, for example, turns dark blue;

b) The solution in the receptacle (e.g. test tube) becomes opaque to room light.

As can be seen, each of the events a) and b) may be characterized as an easily observable visual change. The event times may be recorded in a table—such as that given in the example below. The change in specimen color (e.g. event (a)) may be used as the primary or preferred indicator for a test, according to one embodiment, and the change in opaqueness of the solution may be used as a secondary or back-up indicator for the test. Also, in an alternative embodiment using a molybdate/nitric acid etching/indicating solution as described above, event a) may be described as the specimen either changing color (e.g. to dark blue) or no significant change in color occurring during the time that a control specimen has changed color.

At step 116, the times for each event in each receptacle for each specimen may be compared to make a determination for the unknown test specimen or specimens. The event times for the control specimens may be considered as setting a standard for each of the known coatings that the control specimens represent. Thus, for example, the test may use the test rivet event times and the known rivet standards to determine the coating of the unknown rivet. It should be noted that the time required to turn the specimens (e.g. rivets) dark blue may be preferable as an indicator over the time required for the solution in the receptacles (e.g. test tubes) to become opaque to room light. Although the test may be performed according to a number of different embodiments, the test should normally be performed using known rivets along with test rivets, rather than by comparing a batch of random unknown rivets, for example.

EXAMPLE

In accordance with one embodiment, ten rivets were blind tested, e.g. without the person performing the test knowing beforehand which of the rivets had only alodine or both alodine and sol-gel coating. Results of the event timings referred to above are tabulated below.

| rivet # | rivet blue (mins) | solution opaque (mins) |
|---|---|---|
| 1 | 6 | 26 |
| 2 | 21 | 42 |
| 3 | 20 | 39 |
| 4 | 8 | 29 |
| 5 | 16 | 35 |
| 6 | 8.5 | 28 |
| 7 | 8 | 28 |
| 8 | 21 | 39 |
| 9 | 7 | 28 |
| 10 | 20 | 38 |

By looking at the times required to turn the rivets dark blue, it may become evident that the rivets fall into two groups exhibiting comparable timing: The first group: rivets 1, 4, 6, 7, and 9 had only alodine; and the second group: rivets 2, 3, 5, 8, and 10 had both alodine and sol-gel.

Bare rivets (e.g. deoxidized, scotchbrited, or burnished) will generally react more quickly than the times listed above.

It should be understood, of course, that the foregoing relates to preferred embodiments of the invention and that modifications may be made without departing from the spirit and scope of the invention as set forth in the following claims.

We claim:

1. A method for testing for the presence of a coating, the method comprising:
   testing for the presence of a sol-gel coating on a metal surface;
   placing a test specimen of unknown coating in a solution in a first receptacle;
   placing a conversion-coated control specimen in the solution in a second receptacle, wherein the conversion-coated control specimen has a leached alodine coating;
   placing a sol-gel-coated control specimen in the solution in a third receptacle, wherein the sol-gel-coated control specimen has a leached alodine plus sol-gel coating;
   observing a first length of time for the test specimen to change color;
   observing a second length of time for the conversion-coated control specimen to change color;
   observing a third length of time for the sol-gel-coated control specimen to change color; and
   determining a presence or absence of the coating on the test specimen based on comparison of the first length of time, the second length of time, and the third length of time.

2. A method for testing for the presence of a sol-gel coating, the method comprising:
   placing a mixed solution in a receptacle;
   placing a test specimen of unknown coating in said receptacle; and
   timing an event to make a determination of whether or not the sol-gel coating is present.

3. The method of claim 2 wherein said event is a change in color of the test specimen to blue.

4. The method of claim 2 wherein said event is no change in color of the test specimen after a pre-determined amount of time.

5. The method of claim 2 wherein said event is said mixed solution becoming opaque.

6. The method of claim 2 further comprising steps of:
   placing a sol-gel-coated control specimen in said mixed solution in a second receptacle;
   timing a second event; and
   determining that sol-gel is present on the test specimen of unknown coating if the timing of the event and the timing of the second event are comparable.

7. The method of claim 2 further comprising steps of:
   placing a sol-gel-coated control specimen in said mixed solution in a second receptacle;
   placing an conversion-coated control specimen in said mixed solution in a third receptacle;
   timing a second event;
   timing a third event;
   determining that sol-gel is present on the test specimen of unknown coating if the timing of the event and the timing of the second event are comparable; and
   determining that sol-gel is not present on the test specimen of unknown coating if the timing of the event and the timing of the third event are comparable.

8. The method of claim 2 further comprising a step of:
   forming said mixed solution from an indicating solution and an etching solution.

9. The method of claim 2 wherein said step of placing a mixed solution in a receptacle comprises:
   placing a indicating solution in said receptacle; and
   mixing an etching solution with said indicating solution in said receptacle.

10. The method of claim 2 further comprising a step of:
    preparing an indicating solution from water and an ingredient chosen from the group consisting of: ammonium molybdate, sodium molybdate, and potassium molybdate.

11. The method of claim 2 further comprising a step of:
    preparing an indicating solution from water and an ingredient chosen from the group consisting of the alkali metal molybdates.

12. The method of claim 2 further comprising a step of:
    preparing an indicating solution from water and an ingredient chosen from the group consisting of the alkaline earth metal molybdates.

13. The method of claim 2 further comprising a step of:
    preparing an etching solution from water and an ingredient chosen from the group consisting of: hydrochloric acid, and hydrobromic acid.

14. The method of claim 2 further comprising a step of:
    preparing an etching/indicating solution including nitric acid.

15. A method for testing for the presence of a coating on aluminum, comprising steps of:
    mixing an indicating solution and an etching solution in a plurality of receptacles to form a mixed solution in said plurality of receptacles;
    placing a test specimen of unknown coating in a first receptacle of said receptacles;
    placing a control specimen in a second receptacle of said receptacles; and
    timing a plurality of events to make a determination of whether or not the coating is present on the test specimen.

16. The method of claim 15 wherein the coating tested for is a sol-gel coating.

17. The method of claim 15 wherein said plurality of events includes: a change in color of the entire test specimen to dark blue; and
    a change in color of the entire control specimen to dark blue.

18. The method of claim 15 wherein said plurality of events includes:
    said mixed solution in said first receptacle becoming opaque to room light; and
    said mixed solution in said second receptacle becoming opaque to room light.

19. The method of claim 15 wherein said test specimen and said control specimen are aluminum parts of the same size, type and alloy.

20. The method of claim 17 further comprising steps of:
    placing a second control specimen in a third receptacle of said receptacles;
    wherein said plurality of events includes a change in color of the entire second control specimen to dark blue;
    determining that the test specimen of unknown coating has a like coating to that of the control specimen if the timing of the change in color of the entire test specimen to dark blue and the timing of the change in color of the entire control specimen to dark blue are comparable; and determining that the test specimen of unknown coating has a like coating to that of the second control specimen if the timing of the change in color of the entire test specimen to dark blue and the timing of the change in color of the entire second control specimen to dark blue are comparable.

21. The method of claim 18 further comprising steps of:
placing a second control specimen in a third receptacle of said receptacles;
wherein said plurality of events includes said mixed solution in said third receptacle becoming opaque to room light; and
determining that the test specimen of unknown coating has a like coating to that of the control specimen if the timing of said mixed solution in said first receptacle becoming opaque to room light and the timing of said mixed solution in said second receptacle becoming opaque to room light are comparable; and
determining that the test specimen of unknown coating has a like coating to that of the second control specimen if the timing of said mixed solution in said first receptacle becoming opaque to room light and the timing of said mixed solution in said third receptacle becoming opaque to room light are comparable.

22. The method of claim 15 further comprising steps of:
placing a second control specimen in a third receptacle of said receptacles;
wherein: said test specimen, said control specimen, and said second control specimen are aluminum rivets of the same size, type and alloy;
said control specimen has a sol-gel over conversion coating;
said second control specimen has only a conversion coating; and
said timing step includes determining whether said test rivet has the sol-gel over conversion coating or only the conversion coating.

23. The method of claim 15 further comprising a step of:
preparing said indicating solution by adding 10 g of ammonium molybdate, 4-hydrate in 100 ml of water.

24. The method of claim 15 further comprising a step of:
preparing said etching solution by adding concentrated hydrochloric acid.(HCl) in 1:1 ratio to water.

25. A method for testing for the presence of sol-gel on an aluminum test specimen, comprising steps of:
preparing fresh, weekly, an indicating solution by dissolving 10 g of ammonium molybdate, 4-hydrate in 100 ml of water;
preparing an etching solution by adding hydrochloric acid in 1:1 ratio to water;
using a pipette to place 4 ml of said indicating solution into each of a plurality of receptacles;
adding 2 ml of said etching solution to each of said plurality of receptacles;
mixing said indicating solution and said etching solution in each of said plurality of receptacles to form a mixed solution in each of said plurality of receptacles;
placing a test specimen of unknown coating in said mixed solution in a first receptacle of said plurality of receptacles;
placing a first control specimen in said mixed solution in a second receptacle of said plurality of receptacles;
placing a second control specimen in said mixed solution in a third receptacle of said plurality of receptacles;
wherein: said test specimen, said control specimen, and said second control specimen are aluminum rivets of the same size, type and alloy;
said first control specimen has a sol-gel over conversion coating;
said second control specimen has only a conversion coating;
timing a plurality of events including:
a change in color of the entire test specimen to dark blue;
a change in color of the entire first control specimen to dark blue; and
a change in color of the entire second control specimen to dark blue;
determining that the test specimen of unknown coating has a like coating to that of the first control specimen if the timing of the change in color of the entire test specimen to dark blue and the timing of the change in color of the entire first control specimen to dark blue are comparable; and
determining that the test specimen of unknown coating has a like coating to that of the second control specimen if the timing of the change in color of the entire test specimen to dark blue and the timing of the change in color of the entire second control specimen to dark blue are comparable.

26. The method of claim 25, further including steps of:
testing a control specimen that is a bare rivet; and
determining whether the test specimen of unknown coating is a bare rivet or not.

27. The method of claim 25, further including a step of:
comparing the timing of the change in color of the test specimen to the timing of the change in color of the first control specimen in order to estimate a relative thickness of a sol-gel coating on the test specimen.

28. A method of testing for the presence of a coating of sol-gel, alodine, or sol-gel over alodine on an aluminum aircraft part, the method comprising:
(A) immersing said aluminum aircraft part in a first solution of ammonium molybdate and etching solution;
(B) measuring a first time required for a visual change to occur; and
(C) comparing said first time to a second time required for a similar visual change to occur when an aluminum aircraft part having a known coating of sol-gel, alodine, or sol-gel over alodine is immersed in a second solution having the same composition as said first solution.

29. The method according to claim 28 wherein said visual change is a turning blue.

30. The method according to claim 28 wherein said visual change is a turning opaque.

31. The method according to claim 28 wherein all of said aluminum aircraft parts have the same shape and are made of the same alloy of aluminum.

32. The method according to claim 28 wherein said aluminum aircraft part is tested for the presence of a coating of sol-gel, alodine, and sol-gel over alodine and three aluminum aircraft parts are used in step (C), one coated with only sol-gel, one coated with only alodine, and one coated with sol-gel over alodine.

* * * * *